United States Patent [19]

Ashley, Robert J. et al.

[11] Patent Number: 4,553,971

[45] Date of Patent: Nov. 19, 1985

[54] POUCH-LIKE BAGS FOR CONTAINING LIQUIDS

[75] Inventors: Ashley, Robert J., Faringdon; Bardhan, Nabendu, Abingdon; Peter D. Hardy, Wantage; Keith D. Jeffs, Malmesbury, all of England

[73] Assignee: Metal Box p.l.c., Reading, England

[21] Appl. No.: 568,200

[22] PCT Filed: Mar. 23, 1983

[86] PCT No.: PCT/GB83/00086

§ 371 Date: Nov. 22, 1983

§ 102(e) Date: Nov. 22, 1983

[87] PCT Pub. No.: WO83/03351

PCT Pub. Date: Oct. 13, 1983

[30] Foreign Application Priority Data

Mar. 24, 1982 [GB] United Kingdom ................. 8208683

[51] Int. Cl.[4] ................................................ A61F 7/00

[52] U.S. Cl. .................................... 604/415; 222/107; 383/38

[58] Field of Search ................... 222/92, 94, 107, 106, 222/153, 206, 215, 212, 541, 542; 383/5, 38, 40; 206/807; 604/410, 408, 415, 403

[56] References Cited

U.S. PATENT DOCUMENTS

| | | | |
|---|---|---|---|
| 2,635,788 | 4/1953 | Snyder et al. | 222/107 |
| 3,255,923 | 6/1966 | Soto | 222/80 |
| 3,474,789 | 10/1969 | Soto | 604/415 |
| 3,520,471 | 7/1970 | Faust | 229/56 |
| 4,196,030 | 4/1980 | Ausnit | 222/92 |
| 4,320,789 | 3/1982 | Martin et al. | 222/107 |

FOREIGN PATENT DOCUMENTS

| | | | |
|---|---|---|---|
| 0038312 | 9/1981 | European Pat. Off. . | |
| 2160939 | 6/1973 | Fed. Rep. of Germany . | |
| 3021911 | 2/1982 | Fed. Rep. of Germany . | |
| 1264631 | 5/1961 | France | 383/38 |
| 2020212 | 7/1970 | France . | |
| 2186402 | 2/1973 | France . | |
| 1081900 | 10/1964 | United Kingdom . | |
| 1579065 | 3/1977 | United Kingdom . | |
| 2078199 | 6/1981 | United Kingdom . | |

*Primary Examiner*—H. Grant Skaggs
*Assistant Examiner*—Kenneth Noland
*Attorney, Agent, or Firm*—Burns, Doane, Swecker & Mathis

[57] ABSTRACT

A pouch-like bag for containing a liquid for medical or surgical use has two walls (10, 11) formed by respective plies of flexible plastics material sealed together (at 12) around at least their top and side edges and one or more, folded plies (14) of flexible plastics material of substantially smaller dimensions forming a gusset bottom portion having opposed leaves (16, 17) each of which is sealed (at 18) to the adjacent wall (10, 11). The gusset ply (14) carries one or more elements (21, 22 ) of elastomeric material capable of making an hermetic and liquid-tight seal with a needle, e.g. an administration set needle for a hospital drip-feed system or a hypodermic or injection needle for injecting a drug into the bag contents. The gusset ply (14) is closed by a seal (27) between its leaves to form a sealed compartment which can be opened, either by peeling open the seal (27) or by cutting or tearing, whereupon it forms a substantially flat bottom portion of the bag and presents the elements (21, 22) substantially perpendicular to the walls (10, 11) for insertion of a needle or needles without risk of accidental penetration of the walls.

10 Claims, 15 Drawing Figures

Fig. 4
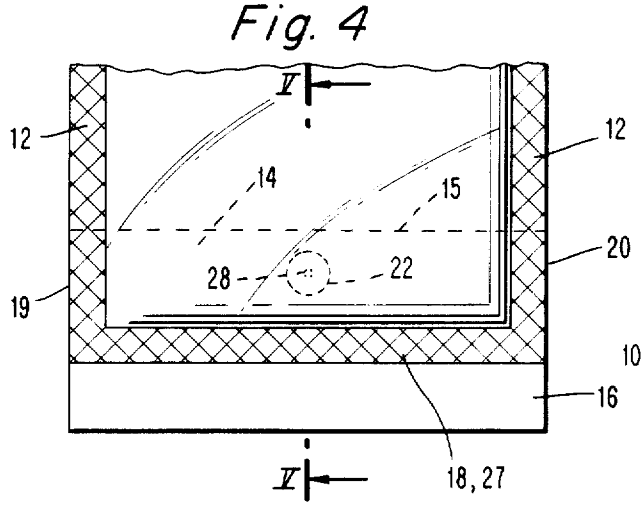
Fig. 5
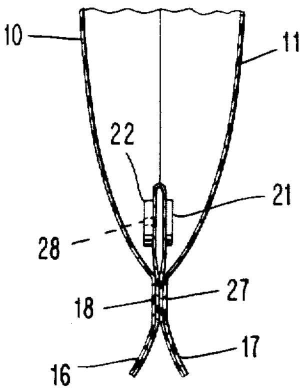
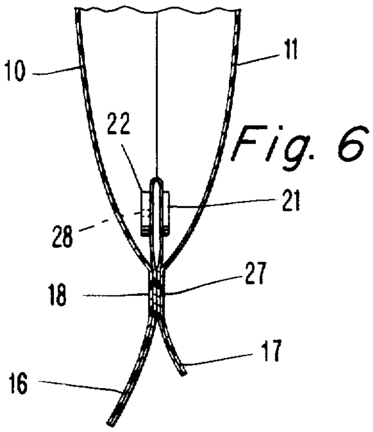
Fig. 6
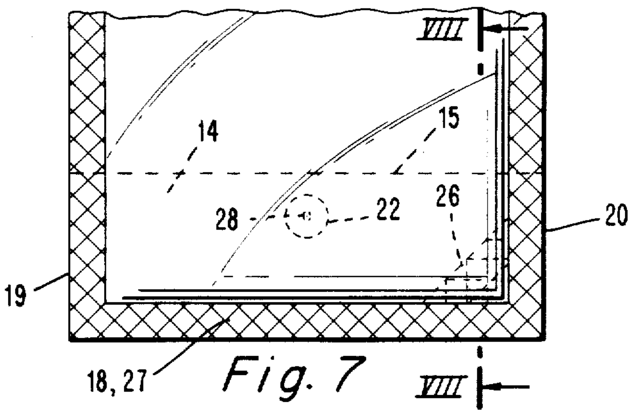
Fig. 7
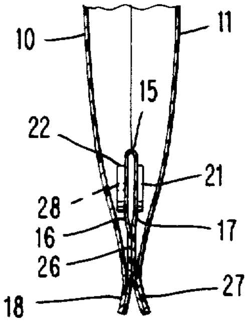
Fig. 8

Fig. 9
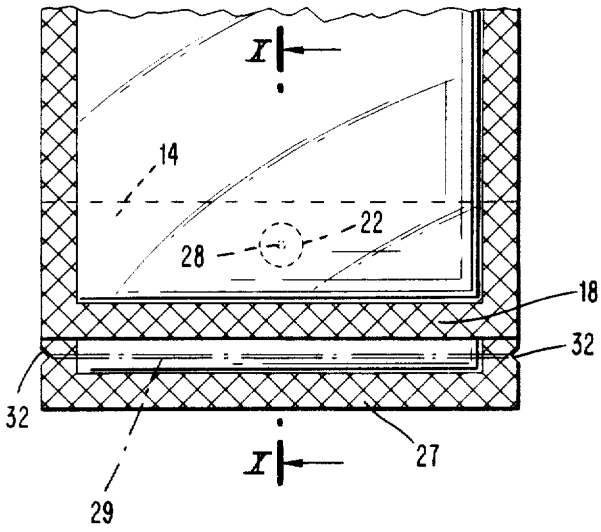
Fig. 10
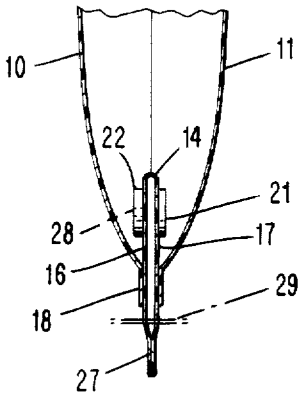
Fig. 11
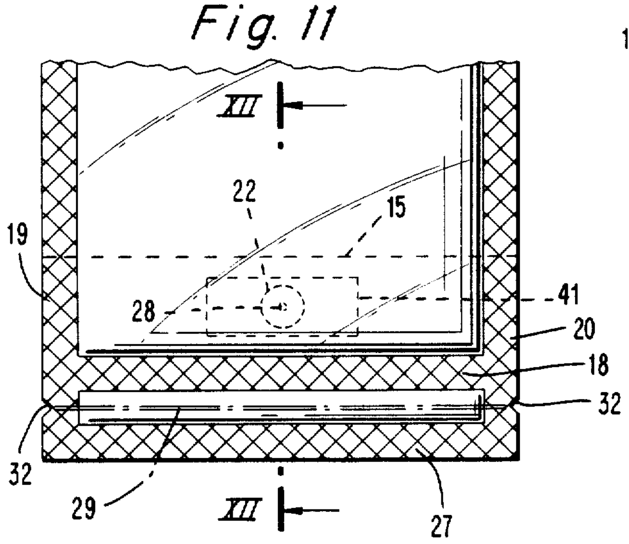
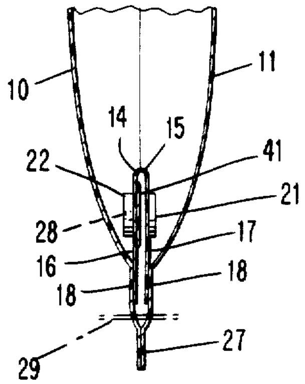
Fig. 12

Fig. 13
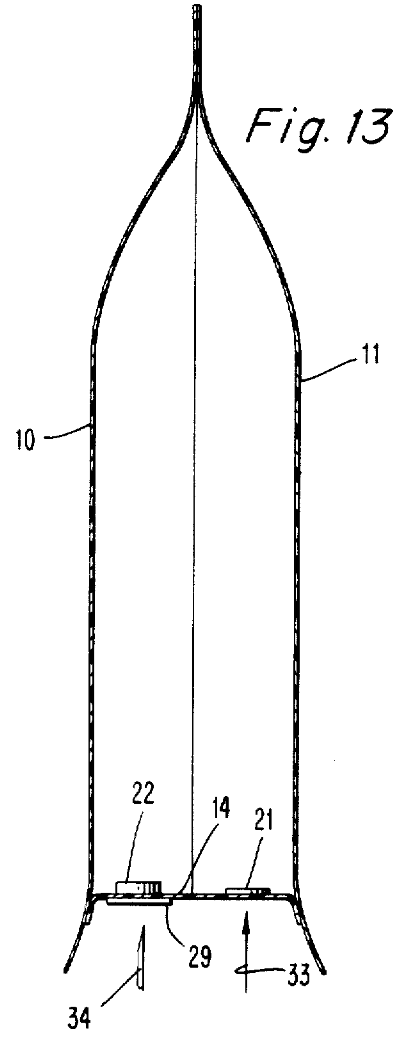
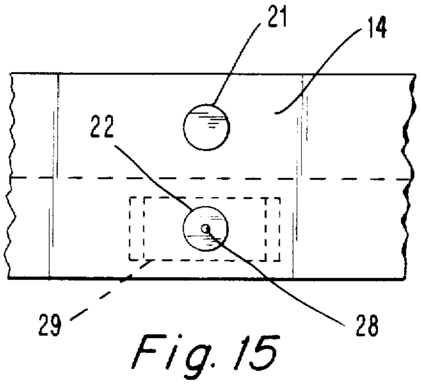
Fig. 15
Fig. 14
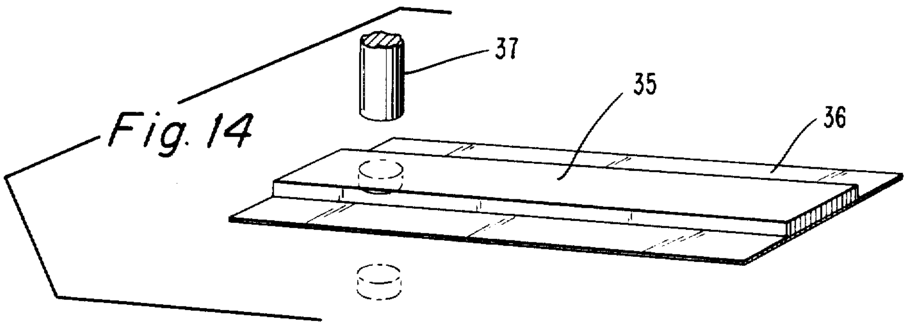

POUCH-LIKE BAGS FOR CONTAINING LIQUIDS

This invention relates to pouch-like bags for containing liquids for medical or surgical use, such as a liquid for intravenous injection by means of a hospital drip feed system. For such use, the bag should be capable of receiving one or more needles for making connection to the bag contents, for example, a dispensing or administration needle which will connect the liquid with the drip feed system and/or an injection or hypodermic needle by which a drug can be injected into the liquid before it is administered to a patient. The formation of formations provided for this purpose should be sterile and protected from contamination. Moreover, it or they should be capable of reliably making an hermetic and liquid-tight seal with a needle inserted therethrough.

Such bags have previously been made with tubular inserts sealed into an edge portion of the bag to form ports for insertion of needles and with sealed tear-off chambers outboard of the ports, as described in British Patent Specification No. 1544811, for example.

In our co-pending British patent application No. 8138586, we have described and claimed a pouch-like bag for containing a liquid for medical or surgical use, the bag having two walls formed by respective plies of flexible plastics material sealed together around their periphery, wherein the bag is provided with an elongate insert of polymeric material which is capable of self-sealing a puncture made transversely through the insert, the insert being sealed between the plies of flexible material so as to extend adjacent to a portion of the bag periphery, and extreme sealed peripheral portions of the plies of flexible material outboard of the insert forming a tearable tag which, when torn off the bag, exposes at least part of the length of the said insert, along a side face thereof, so as to allow an injection or dispensing needle access to penetrate transversely through the insert and into the bag.

European patent application No. 0038312 describes a package suitable for storage of preparations for parenteral administration, e.g. intravenous infusion solutions, which is designed to protect the contents from the influence of light, microbial contamination and gas transport in either direction but which makes possible a visual control of the contents before the package is used. For these purposes, the package is made of a light-proof outer bag and a light permeable inner bag arranged inside the outer bag. The outer bag and the inner bag are each sealed at one of their ends and are bonded around their periphery close to their outer end, and the two bags extend over this bond and are then commonly joined and sealed. By opening one of the end seals in the outer bag, the inner bag can be turned out of the outer bag, and the contents of the package can be observed visually through the inner bag. A tapping device of conventional design may be arranged in the wall of the inner bag so as to be accessible when the inner bag has been turned out of the outer bag.

It is an object of the present invention to provide an economical and effective construction of a bag for containing liquids for medical or surgical use, particularly a liquid for intravenous injection by means of a hospital drip feed system.

According to the present invention, a pouch-like bag for this purpose has two walls formed by respective plies of flexible plastics material sealed together around at least their top and side edges, and a third, folded ply of flexible plastics material which is disposed between the walls of the bag to form a gusset fold having opposed leaves sealed to the adjacent walls of the bag and which carries one or more elements for receiving a needle for making connection with the bag contents and which is closed below the element or elements to form a sealed compartment protecting the or each element from contamination, and is characterised in that the third or gusset ply is substantially smaller than the walls of the bag, so that when the sealed compartment is opened the gusset ply forms a substantially flat bottom of the bag and presents the element or elements substantially perpendicular to the walls of the bag for insertion of a needle or needles without risk of accidental penetration of the walls.

In one construction of the bag, the seals between the leaves of the gusset ply and the adjacent walls of the bag coincide with a peelable seal between the leaves of the gusset ply which closes the sealed compartment, and the leaves of the gusset ply and/or the walls of the bag extend below the coincident seals to form gripping means to enable the peelable seal to be opened. To ensure that the peelable seal can be peeled open, the material of the gusset ply or the nature of the sealing surfaces is selected or modified to ensure that the seal has the necessary relatively low strength.

In a second construction, the sealed compartment is adapted to be opened by severance of a lower marginal portion of the bag along a severance line disposed below the seals between the opposed leaves of the gusset ply and the adjacent walls of the bag. The severance line is preferably disposed so that only two thicknesses of the flexible plastics material need to be torn to open the sealed compartment. For this purpose, either the walls of the bag do not extend as far as the severance line, which is formed in the leaves of the gusset ply above a seal between the leaves which closes the sealed compartment, or the leaves of the gusset ply do not extend as far as the severance line, which is formed in the walls of the bag above a seal between the walls which closes the sealed compartment.

Preferably the or each needle-receiving element is of elastomeric material capable of making an hermetic and liquid-tight seal with a needle inserted therethrough. A peelable protective strip may be attached to the gusset ply within the gusset fold to provide temporary protection for the area of the gusset fold bottom of the bag adjacent one or more of said needle-receiving elements after the sealed compartment has been opened and before a needle is inserted. The or each element may be of any suitable shape, for example, circular, square or in the form of an elongate strip. It may be attached to the inner or outer surface of the gusset ply (in relation to the gusset fold); where the gusset ply has a plurality of layers, it may be located between those layers. It is preferably disposed to project from the gusset ply outwardly, but not inwardly, of the gusset fold, so as not to impede the leaves of the gusset ply from folding fully together.

Specific embodiments of the invention will now be described in more detail by way of example and with reference to the accompanying drawings, in which.

Figure 3:
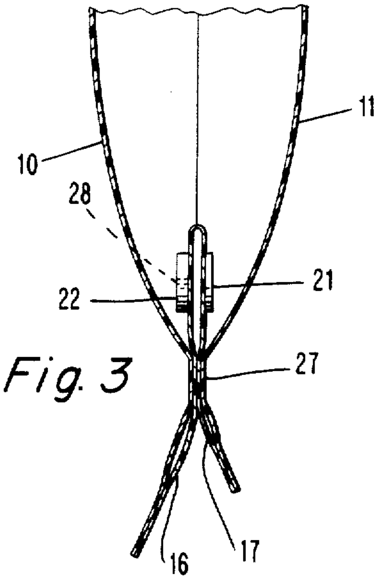
FIG. 3 is a cross-sectional view similar to FIG. 2 showing a modification.

FIG. 4 is a diagrammatic elevation of the lower part of a modified form of bag, FIG. 5 is a diagrammatic sectional view on line V—V of FIG. 4, FIG. 6 is a similar sectional view of a modification corresponding to that of FIG. 3, FIG. 7 is a diagrammatic elevation of a lower part of another form of bag in accordance with the invention, FIG. 8 is a sectional view on line VIII—VIII of FIG. 7, FIG. 9 is a diagrammatic elevation of the lower part of yet another form of bag in accordance with the invention, FIG. 10 is a sectional view on line X—X of FIG. 9, FIG. 11 is a view similar to FIG. 9 and showing the lower part of a further bag in accordance with the invention, FIG. 12 is a sectional view on line XII—XII of FIG. 11, FIG. 13 is a cross-sectional view of the bag of FIGS. 11 and 12, showing the bag after cutting between the lower seals to expose the needle-insertion elements, FIG. 14 is a diagrammatic illustration of the production of the needle-insertion elements, and FIG. 15 illustrates the mounting of the needle-insertion elements on a ply of plastics material which is to form the gusset ply.

Figure 1:
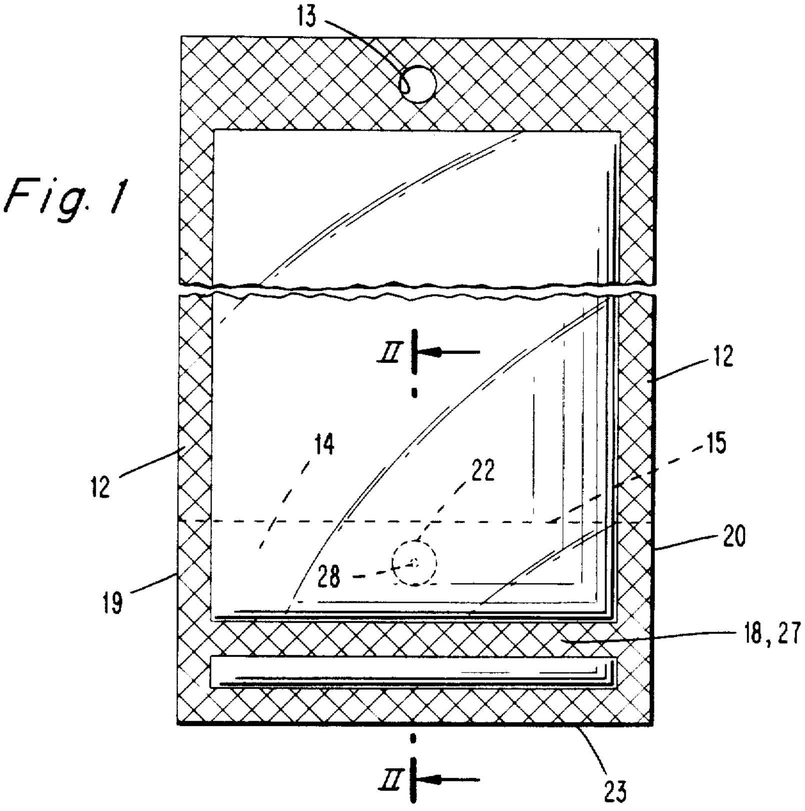
FIG. 1 is a diagrammatic elevation of a bag in accordance with the invention.
Figure 2:
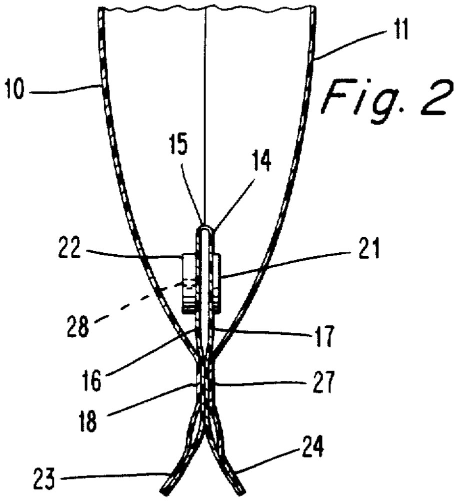
FIG. 2 is a diagrammatic cross-section on line II—II of FIG. 1.

As shown diagrammatically in FIGS. 1 and 2, a bag has two walls 10,11 formed by respective plies of flexible plastics material sealed together at 12 around their top and side edges. A suspension hole 13 is punched in the top seal and this area may be reinforced by including an insert of strengthening material, if desired. In the lower part of the bag, a third or gusset ply 14 of flexible plastics material folded along line 15 is disposed between the walls 10,11, and each leaf 16,17 of the gusset ply 14 is heat-sealed to the adjacent wall 10,11 along line 18. The gusset ply 14 is also heat-sealed between the walls 10,11 at the edges of the bag as shown at 19,20. The gusset ply 14 is substantially smaller than the walls 10,11 and thus forms for the bag a gusset bottom which is closed at its top along the fold line 15 and closed along its sides by the seals 19,20.

The gusset ply 14 carries two elements 21,22 of elastomeric material, on opposite sides of the fold line 15 and outside the gusset fold (but within the bag interior). The elastomeric elements are shown as flat circular discs secured to the gusset ply 14. Element 21 is designed to be capable of self-sealing a puncture made therethrough by a hypodermic needle, e.g. for inserting a drug into liquid contained in the bag. Element 22 is designed to be capable of sealing around an administration needle forced therethrough, and may be formed with a hole 28 for guiding the needle. Usually, as shown, the element 22 will be made of thicker material than the element 21 to provide adequate retention of the administration needle.

Below the elements 21,22 the two leaves 16,17 of the gusset ply 14 are additionally heat-sealed together at 27 so as to form the gusset fold into a sealed compartment in which the access points of the needles 21,22 are disposed and protected from contamination. In the example illustrated in FIGS. 1 and 2, the seal 27 between the leaves 16,17 coincides with the seals 18 between the respective walls 10,11 and the leaves 16,17.

In order to enable the sealed compartment to be opened to provide access to the elements 21,22 when required for insertion of a hypodermic or administration needle, the side seals 19,20 and bottom seal 27 between the leaves 16,17 are peelable, the material of the gusset ply 14 being chosen, or its surface being treated, so as to ensure that any seal made with itself is of sufficiently low strength to be peelable. To provide gripping means for peeling open the seals, the walls 10,11 and the leaves 16,17 are extended beyond the seal line 18, their extremities being sealed together at 23,24. If desired, the gusset ply may be cut away locally, e.g. by notching, along the sides of the bag within the seals 19,20 so as to allow the walls 10,11 to be directly heat-sealed together in that locality. In this way the peelability of the seals 19,20 may be limited to a transverse line lying below the fold line 15 of the gusset ply. When the sealed compartment has thus been opened, the gusset ply 14 forms a substantially flat bottom of the bag and presents the elements 21,22 substantially perpendicular to the walls of the bag for insertion of a needle or needles without risk of accidental penetration of the walls.

FIG. 3 illustrates a modification of the construction of FIGS. 1 and 2, in which the wall 10 and the corresponding leaf 16 are extended further than the walls 11 and leaf 17 to facilitate gripping of the respective leaves for peeling open the seal.

FIGS. 4, 5 and 6 illustrate an embodiment similar to that of FIGS. 1, 2 and 3, but in which the walls 10,11 do not extend beyond the seals 18,27. The leaves 16,17 extend beyond the seals 18,27 as before, and provide gripping means for peeling open the seals between them.

FIGS. 7 and 8 illustrate an embodiment which is similar to those of FIGS. 1 to 6 except that the extensions of the walls 10,11 and leaves 16,17 beyond the seal 27 are omitted, and the seal 27 is taken diagonally, at 26, across a bottom corner of the bag instead of following the seals 18 in that locality. Two free corner tabs 25 are thereby provided for the user to grasp when opening the bag.

FIGS. 9 to 12 illustrate alternative embodiments which are not intended for use with a peelable seal, but are provided with a severance line for opening the sealed compartment.

In the embodiment of FIGS. 9 and 10, the lower extremities of the walls 10,11 are sealed to the respective leaves 16,17 at seals 18 as before. The leaves 16 and 17 project below the seals 18 and are sealed together at their lower extremities at 27. To open the sealed compartment to provide needle access to the elements 21,22, the bag is torn or cut along a severance line 29 defined by tear initiating formations 32 (cuts or notches) between the seals 18 and 27.

FIGS. 11 and 12 illustrate a second embodiment having a severable portion. In this case the walls 10,11 are continued below the seals 18, which are made with the lower extremities of the gusset ply 14. The walls 10,11 are themselves sealed together at 27 along their lower extremities to form a sealed compartment with the gusset ply. Tear initiating formations 32 are formed in the walls 10,11 below the seals 18 to assist the opening of this compartment for use.

In use of each of the bags shown in the drawings, the sealed compartment formed within the gusset fold is opened by the user by manually peeling the compartment open along the seals 27,19 and 20 or, as appropriate, by severing the bag along line 29 as described. FIG. 13 shows the bag of FIGS. 11 and 12 when opened, but it will be understood that the other embodiments generally correspond.

From FIG. 13 it will be seen that the opening of the sealed compartment allows freedom for the base region of the bag to open out under the weight of the liquid contents, so that the gusset ply 14 generally adopts the flat condition shown. The needle-insertion elements 21,22 are thereby presented side-by-side for easy access by their respective hypodermic and administration needles. As indicated at 33,34, the needles are forced into the bag through the gusset ply material and the appropriate element, in a direction generally perpendicular to the gusset ply, without risk of accidental penetration of the walls of the bag.

In those bags in which the gusset fold is still closed at its ends along the seals 19,20, the flat, element-carrying part of the gusset ply will be surrounded by a skirt. By suitable arrangement this skirt may serve as a standing edge on which the bag may be stood upright, with the gusset ply held clear of the supporting surface. If desired, additional inclined heat seals may be made across the bag for improving the standing ability of the bag (when open) by controlling the shape adopted by the base region.

FIG. 14 illustrates one way in which the elements 21,22 may be prepared. They may be made from an elastomeric paste based on natural rubber or silicone rubber, being a single component or pre-mixed from a two part system including a cross-linking agent. They may be of any suitable shape, circular elements being illustrated as being generally most convenient.

The thickness of rubber is selected to ensure that the injection needle element will self seal effectively when the needle is withdrawn, and the administration needle element will exert sufficient grip on the administration needle to grip it and retain it and prevent leakage during administration. The elements may therefore be of differing formulations and differing thicknesses, e.g. 1 mm thick for the injection needle element and 3 mm for the administration needle element. To produce the elements, a layer 35 of the elastomeric material is applied by conventional coating means to a treated surface of a polyolefin film 36 which is formulated so as to be heat sealable to the appropriate surface of the gusset web 14. After curing the elastomer, the elements are punched out by a punch shown diagrammatically at 37 and heat sealed through their backing film 36 to the gusset ply 14 as shown in FIG. 15, on either side of the centre line 15.

A further way in which the elements 21,22 may be prepared is to thermoform a web of the gusset ply 14 with shallow cavities, one for each element. The elements themselves are then located in the cavities either as preformed discs or moulded in situ from a suitable elastomer. The elements are thereafter encapsulated within the cavities by a second web of material which is bonded to the first layer so as to close the cavities and form a second layer of the gusset ply. Preferably, as with the embodiments particularly described above, the elements are located to project outside the gusset ply (but within the bag interior), so that they do not impede the gusset leaves 16,17 from being folded fully together.

Manufacture of the bags described above with reference to the drawings is exemplified by the following description of a preferred method of manufacturing bags of the particular form shown in FIGS. 11 and 12. Two continuous webs of plastics material to form the walls 10,11 are fed horizontally together on either side of a further, longitudinally folded web which is destined to form the gusset plies 14 of the bags and which accordingly carries pairs of elements 21,22 at regular intervals along its length. Continuous heat seals 18 are then made between the outer webs and the lower extremities of the folded web while a plate is positioned within the folded web to prevent its leaves from being heat-sealed together. The three webs then move together beyond the end of the plate, and a further continuous heat seal is made along the lower extremities of the outer webs to form the heat seals 27. Finally the webs are heat sealed transversely at intervals between the pairs of elements 21,22, the tear-initiating formations 32 are formed, and the individual bags are separated from one another by severing the webs along the transverse seals. The bags are subsequently filled with liquid, closed by top seals 30 (FIG. 1), and suspension holes 13 punched within the seal closure area.

In order to maintain substantially aseptic conditions after it has been opened, each of the bags described above may have a peelable strip attached to the interior surface of the gusset ply so as to provide a protective cover over the entry point of an administration and/or hypodermic needle until immediately before the needle is inserted. One such strip is shown in FIGS. 11 to 13 in relation to administration needle element 22, and indicated by the reference numeral 41. Strip 41 is attached to the gusset ply 14 at a suitable time before the gusset ply is incorporated into the bag.

In a modification of each of the described bags, one or both of the needle-insertion elements is attached to the inner surface of the gusset ply and disposed to lie within the gusset fold. A protective strip as described in the preceding paragraph may then be advantageously provided as a separator between the elements.

A bag in accordance with the invention may have its walls 10,11 made of a single layer of plastics material or of laminated construction. In one possible wall structure an outer heat-resistant film such as nylon, a polyester or polypropylene is bonded to a heat-sealable inner ply, typically a polyolefin or modified polyolefin. The materials are clear and transparent and capable of withstanding steam sterilisation. The gusset ply may be of a similar material, laminated or otherwise, and may include or be formed of a blend of polyolefins. In one possible construction the walls and the gusset ply are integrally formed from a single sheet of plastics material folded longitudinally into W formation.

Although each of the bags particularly described has two needle-insertion elements carried by the same gusset ply in mutual opposition, the invention also extends to bags having only one element, for example in the form of an elongate strip on or in one of the leaves of the gusset ply, and to bags having two or more elements. Where two or more elements are provided they may be disposed so as to be spaced apart (i.e. non-overlapping) in the same gusset ply, or they may be carried by separate gusset plies. In one such latter arrangement a bag has two gusset plies each carrying one element, the plies being individually disposed at the bottom corners of the bag so as to extend, at an inclination to the centre-line of the bag, from the bottom edge to respective side edges of the bag.

We claim:

1. A pouch-like bag for containing a liquid for medical or surgical use, the bag having two walls formed by respective plies of flexible plastics material sealed together around at least their top and side edges and one or more additional, folded piles of flexible plastics material disposed between the walls of the bag to form a gusset fold having opposed leaves sealed to the adjacent walls of the bag and which carries one or more elements for receiving a needle for making connection with the bag contents and which is closed to form a sealed compartment protecting the or each element which it carries from contamination, characterised in that said one or more additional, folded plies being substantially smaller than the walls of the bag, so that when the sealed compartment is opened said one or more folded plies form a substantially flat bottom portion of the bag extending substantially perpendicular to the walls of the bag and presenting the element or elements for insertion of a needle or needles in a direction substantially parallel to the walls of the bag so as to avoid risk of accidental penetration of the walls.

2. A bag according to claim 1 characterised in that the seals between the leaves of the gusset ply and the adjacent walls of the bag coincide with a peelable seal between the leaves of the gusset ply which closes the sealed compartment, and the leaves of the gusset ply and/or the walls of the bag extend below the coincident seals to form gripping means to enable the peelable seal to be opened.

3. A bag according to claim 1 characterised in that the sealed compartment is adapted to be opened by severance of a lower marginal portion of the bag along a severance line disposed below the seals between the opposed leaves of the gusset ply and the adjacent walls of the bag.

4. A bag according to claim 3 characterised in that the walls of the bag do not extend as far as the severance line, which is formed in the leaves of the gusset ply above a seal between the leaves which closes the sealed compartment.

5. A bag according to claim 2 characterised in that the leaves of the gusset ply do not extend as far as the severance line, which is formed in the walls of the bag above a seal between the walls which closes the sealed compartment.

6. A bag according to any one of the preceding claims characterised in that the or each needle-receiving element is of elastomeric material capable of making an hermetic and liquid-tight seal with a needle inserted therethrough.

7. A bag according to claim 1 characterised in that a peelable protective strip is attached to the gusset ply within the gusset fold to provide temporary protection for the area of the gusset fold bottom of the bag adjacent one or more of said needle-receiving elements after the sealed compartment has been opened and before a needle is inserted.

8. A bag according to claim 1 characterised in that the or each needle-receiving element is attached to the outer surface of the gusset ply in relation to the gusset fold (i.e. the inside of the bag) through a backing layer of plastics material.

9. A bag according to claim 1, characterised in that the gusset ply has a plurality of layers and the or each needle-receiving element is located between two of said layers.

10. A bag according to claim 1, characterised by two of said needle-receiving elements disposed one on each side of the fold line of the gusset ply.

* * * * *